United States Patent [19]
Lee

[11] Patent Number: 5,843,726
[45] Date of Patent: Dec. 1, 1998

[54] EXPRESSION OF A CLEAVABLE FUSION PROTEIN COMPRISING A SOLUBLE HUMAN ERYTHROPOIETIN RECEPTOR PROTEIN FRAGMENT

[76] Inventor: Jong Y. Lee, 514 Huron Blvd., S.E., #A-11, Minneapolis, Minn. 55414

[21] Appl. No.: 850,293

[22] Filed: May 5, 1997

Related U.S. Application Data

[63] Continuation of Ser. No. 499,643, Jul. 7, 1995, abandoned, which is a continuation of Ser. No. 106,815, Aug. 16, 1993, abandoned.

[51] Int. Cl.⁶ .......................... C12N 15/12; C07K 14/715
[52] U.S. Cl. ................ 435/69.7; 435/320.1; 435/252.33; 536/23.4; 530/350; 530/395
[58] Field of Search ..................................... 530/350, 395; 435/320.1, 23.5, 69.7, 252.33; 536/23.4

[56] References Cited

U.S. PATENT DOCUMENTS 4,558,005  12/1985  Goldwassen et al. .

OTHER PUBLICATIONS

Chiba et al., Biochemical Biophysical Research Comm. 1992 184: 485–490.
Jones et al., Blood, vol. 76, No. 1, (Jul.1), 1990: pp. 31–35.
Winkelmann et al., Blood, vol. 76, No. 1 (Jul.), 1990: pp. 24–30.
Penny & Forget, Genomics 11:974–980 (1991).
Noguchi et al., Blood, vol. 78, No. 10 (Nov. 15) 1991: pp. 2548–2556.
D'Andrea & Zon, J. Clin Invest., vol. 86 (Sep. 1990): pp. 681–687.
Harris et al., J. Biol. Chem., vol. 267, 15205–09 (1992).
D'Andrea et al., Blood, vol. 75, 1990: pp. 874–880.
Smith, D. B., et al. (1988) *Gene* 67: 31–40 (Medline abstract only provided).
Mulcahy et al. (1991) *J. Cell. Biochem.*, Suppl. 0 (15 Part F): p. 146 (Abst. Keystone Symp., 8–26 Mar. 1991).

*Primary Examiner*—David L. Fitzgerald
*Attorney, Agent, or Firm*—Fish & Richardson P.C., P.A.

[57] ABSTRACT

An *E. coli* recombinant plasmid expressing a fusion protein having the human erythropoietin receptor extracellular domain is disclosed. A purified fusion protein produced from such a vector is also disclosed, the fusion protein having a cleavage site suitable for separating the erythropoietin receptor extracellular domain from the remainder of the fusion protein. Antibodies having specific binding affinity for a purified extracellular domain polypeptide are also disclosed. The purified human erythropoietin receptor fragment polypeptide binds erythropoietin. The articles, compositions and methods of the invention are useful for studying ligand binding to erythropoietin receptor and for quantitating the amounts of erythropoietin receptor, as well as for understanding receptor structure and signal transduction.

4 Claims, 6 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: synthetic DNA ( i i i ) HYPOTHETICAL: NO ( i v ) ANTI-SENSE: NO ( i x ) FEATURE:
        ( A ) NAME/KEY: BamH1 linker at 5'end followed by sequence
        for amino acids 25 through 29 of the full length human
        Epor protein. Forward primer for Sequence ID No. 2."

( x i ) SEQUENCE DESCRIPTION: SEQ ID NO:1:

```
T T G G A T C C   G C G   C C C   C C G   C C T       A   A C                                    2 3
                  A l a   P r o   P r o   P r o
                    1
```

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: synthetic DNA ( i i i ) HYPOTHETICAL: NO ( i v ) ANTI-SENSE: NO ( i x ) FEATURE:
        ( A ) NAME/KEY: EcoR1 linker followed by sequence complementary
        to coding sequence for amino acids 226 through 222 of
        full length human EpoR protein. Reverse primer for
        Sequence ID No. 1.

( x i ) SEQUENCE DESCRIPTION: SEQ ID NO:2:

```
T G A A T T C G G G   G T C C A G G T C G   C T                                                  2 2
```

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: NO ( i v ) ANTI-SENSE: NO ( v i ) ORIGINAL SOURCE:
        ( A ) ORGANISM: Homo sapiens ( v i i ) IMMEDIATE SOURCE:
        ( B ) CLONE: pGEX-2T, Pharmacia (Mechanicsburg, PA)

( i x ) FEATURE:

( A ) NAME/KEY: Thrombin Cleavage Site in plasmid vector
                        pGEX-2T."

( x ) PUBLICATION INFORMATION:
           ( A ) AUTHORS: Smith, D.B.
                        Johnson, K.S.
           ( B ) TITLE: Single-step purification of polypeptides
                        expressed in Escherichia coli as fusions with
                        glutathione- S-transferase
           ( D ) VOLUME: 67
           ( F ) PAGES: 31-40
           ( G ) DATE: 1988

( x i ) SEQUENCE DESCRIPTION: SEQ ID NO:3:

```
CTG  GTT  CCG  CGT  GGA     T  CC                                                    18
Leu  Val  Pro  Arg  Gly
  5
```

( 2 ) INFORMATION FOR SEQ ID NO:4:

( i ) SEQUENCE CHARACTERISTICS:
           ( A ) LENGTH: 1527 base pairs
           ( B ) TYPE: nucleic acid
           ( C ) STRANDEDNESS: double
           ( D ) TOPOLOGY: linear ( x ) PUBLICATION INFORMATION:
           ( A ) AUTHORS: Winkelmann , J. C., et al.
           ( C ) JOURNAL: Blood
           ( D ) VOLUME: 76
           ( E ) ISSUE: 1
           ( F ) PAGES: 24-30
           ( G ) DATE: 1990

( x ) PUBLICATION INFORMATION:
           ( A ) AUTHORS: Jones, S.S., et al.
           ( C ) JOURNAL: Blood
           ( D ) VOLUME: 76
           ( E ) ISSUE: 1
           ( F ) PAGES: 31-35
           ( G ) DATE: 1990

( x ) PUBLICATION INFORMATION:
           ( A ) AUTHORS: Noguchi, C.T., et al.
           ( C ) JOURNAL: Blood
           ( D ) VOLUME: 78
           ( E ) ISSUE: 10
           ( F ) PAGES: 2548-2556
           ( G ) DATE: 1991

( x i ) SEQUENCE DESCRIPTION: SEQ ID NO:4:

```
ATG  GAC  CAC  CTC  GGG  GCG  TCC  CTC  TGG  CCC  CAG  GTC  GGC  TCC  CTT  TGT       48
Met  Asp  His  Leu  Gly  Ala  Ser  Leu  Trp  Pro  Gln  Val  Gly  Ser  Leu  Cys
  1                   5                  10                  15

CTC  CTG  CTC  GCT  GGG  GCC  GCC  TGG  GCG  CCC  CCG  CCT  AAC  CTC  CCG  GAC       96
Leu  Leu  Leu  Ala  Gly  Ala  Ala  Trp  Ala  Pro  Pro  Pro  Asn  Leu  Pro  Asp
                20                       25                       30

CCC  AAG  TTC  GAG  AGC  AAA  GCG  GCC  TTG  CTG  GCG  GCC  CGG  GGG  CCC  GAA      144
Pro  Lys  Phe  Glu  Ser  Lys  Ala  Ala  Leu  Leu  Ala  Ala  Arg  Gly  Pro  Glu
           35                            40                       45

GAG  CTT  CTG  TGC  TTC  ACC  GAG  CGG  TTG  GAG  GAC  TTG  GTG  TGT  TTC  TGG      192
Glu  Leu  Leu  Cys  Phe  Thr  Glu  Arg  Leu  Glu  Asp  Leu  Val  Cys  Phe  Trp
      50                       55                       60

GAG  GAA  GCG  GCG  AGC  GCT  GGG  GTG  GGC  CCG  GGC  AAC  TAC  AGC  TTC  TCC      240
Glu  Glu  Ala  Ala  Ser  Ala  Gly  Val  Gly  Pro  Gly  Asn  Tyr  Ser  Phe  Ser
 65                       70                       75                       80

TAC  CAG  CTC  GAG  GAT  GAG  CCA  TGG  AAG  CTG  TGT  CGC  CTG  CAC  CAG  GCT      288
Tyr  Gln  Leu  Glu  Asp  Glu  Pro  Trp  Lys  Leu  Cys  Arg  Leu  His  Gln  Ala
                     85                       90                       95

CCC  ACG  GCT  CGT  GGT  GCG  GTG  CGC  TTC  TGG  TGT  TCG  CTG  CCT  ACA  GCC      336
Pro  Thr  Ala  Arg  Gly  Ala  Val  Arg  Phe  Trp  Cys  Ser  Leu  Pro  Thr  Ala
```

-continued

```
                       100                          105                           110
GAC  ACG  TCG  AGC  TTC  GTG  CCC  CTA  GAG  TTG  CGC  GTC  ACA  GCA  GCC  TCC       384
Asp  Thr  Ser  Ser  Phe  Val  Pro  Leu  Glu  Leu  Arg  Val  Thr  Ala  Ala  Ser
          115                      120                      125

GGC  GCT  CCG  CGA  TAT  CAC  CGT  GTC  ATC  CAC  ATC  AAT  GAA  GTA  GTG  CTC       432
Gly  Ala  Pro  Arg  Tyr  His  Arg  Val  Ile  His  Ile  Asn  Glu  Val  Val  Leu
     130                      135                      140

CTA  GAC  GCC  CCC  GTG  GGG  CTG  GTG  GCG  CGG  TTG  GCT  GAC  GAG  AGC  GGC       480
Leu  Asp  Ala  Pro  Val  Gly  Leu  Val  Ala  Arg  Leu  Ala  Asp  Glu  Ser  Gly
145                      150                      155                      160

CAC  GTA  GTG  TTG  CGC  TGG  CTC  CCG  CCG  CCT  GAG  ACA  CCC  ATG  ACG  TCT       528
His  Val  Val  Leu  Arg  Trp  Leu  Pro  Pro  Pro  Glu  Thr  Pro  Met  Thr  Ser
                    165                      170                      175

CAC  ATC  CGC  TAC  GAG  GTG  GAC  GTC  TCG  GCC  GGC  AAC  GGC  GCA  GGG  AGC       576
His  Ile  Arg  Tyr  Glu  Val  Asp  Val  Ser  Ala  Gly  Asn  Gly  Ala  Gly  Ser
               180                      185                      190

GTA  CAG  AGG  GTG  GAG  ATC  CTG  GAG  GGC  CGC  ACC  GAG  TGT  GTG  CTG  AGC       624
Val  Gln  Arg  Val  Glu  Ile  Leu  Glu  Gly  Arg  Thr  Glu  Cys  Val  Leu  Ser
          195                      200                      205

AAC  CTG  CGG  GGC  CGG  ACG  CGC  TAC  ACC  TTC  GCC  GTC  CTC  GCG  CGT  ATG       672
Asn  Leu  Arg  Gly  Arg  Thr  Arg  Tyr  Thr  Phe  Ala  Val  Leu  Ala  Arg  Met
     210                      215                      220

GCT  GAG  CCG  AGC  TTC  GGC  GGC  TTC  TGG  AGC  GCC  TGG  TCG  GAG  CCT  GTG       720
Ala  Glu  Pro  Ser  Phe  Gly  Gly  Phe  Trp  Ser  Ala  Trp  Ser  Glu  Pro  Val
225                      230                      235                      240

TCG  CTG  CTG  ACG  CCT  AGC  GAC  CTG  GAC  CCC  CTC  ATC  CTG  ACG  CTC  TCC       768
Ser  Leu  Leu  Thr  Pro  Ser  Asp  Leu  Asp  Pro  Leu  Ile  Leu  Thr  Leu  Ser
                    245                      250                      255

CTC  ATC  CTC  GTG  GTC  ATC  CTG  GTG  CTG  CTG  ACC  GTG  CTC  GCG  CTG  CTC       816
Leu  Ile  Leu  Val  Val  Ile  Leu  Val  Leu  Leu  Thr  Val  Leu  Ala  Leu  Leu
               260                      265                      270

TCC  CAC  CGC  CGG  GCT  CTG  AAG  CAG  AAG  ATC  TGG  CCT  GGC  ATC  CCG  AGC       864
Ser  His  Arg  Arg  Ala  Leu  Lys  Gln  Lys  Ile  Trp  Pro  Gly  Ile  Pro  Ser
          275                      280                      285

CCA  GAG  AGC  GAG  TTT  GAA  GGC  CTC  TTC  ACC  ACC  CAC  AAG  GGT  AAC  TTC       912
Pro  Glu  Ser  Glu  Phe  Glu  Gly  Leu  Phe  Thr  Thr  His  Lys  Gly  Asn  Phe
     290                      295                      300

CAG  CTG  TGG  CTG  TAC  CAG  AAT  GAT  GGC  TGC  CTG  TGG  TGG  AGC  CCC  TGC       960
Gln  Leu  Trp  Leu  Tyr  Gln  Asn  Asp  Gly  Cys  Leu  Trp  Trp  Ser  Pro  Cys
305                      310                      315                      320

ACC  CCC  TTC  ACG  GAG  GAC  CCA  CCT  GCT  TCC  CTG  GAA  GTC  CTC  TCA  GAG      1008
Thr  Pro  Phe  Thr  Glu  Asp  Pro  Pro  Ala  Ser  Leu  Glu  Val  Leu  Ser  Glu
                    325                      330                      335

CGC  TGC  TGG  GGG  ACG  ATG  CAG  GCA  GTG  GAG  CCG  GGG  ACA  GAT  GAT  GAG      1056
Arg  Cys  Trp  Gly  Thr  Met  Gln  Ala  Val  Glu  Pro  Gly  Thr  Asp  Asp  Glu
               340                      345                      350

GGC  CCC  CTG  CTG  GAG  CCA  GTG  GGC  AGT  GAG  CAT  GCC  CAG  GAT  ACC  TAT      1104
Gly  Pro  Leu  Leu  Glu  Pro  Val  Gly  Ser  Glu  His  Ala  Gln  Asp  Thr  Tyr
          355                      360                      365

CTG  GTG  CTG  GAC  AAA  TGG  TTG  CTG  CCC  CGG  AAC  CCG  CCC  AGT  GAG  GAC      1152
Leu  Val  Leu  Asp  Lys  Trp  Leu  Leu  Pro  Arg  Asn  Pro  Pro  Ser  Glu  Asp
     370                      375                      380

CTC  CCA  GGG  CCT  GGT  GGC  AGT  GTG  GAC  ATA  GTG  GCC  ATG  GAT  GAA  GGC      1200
Leu  Pro  Gly  Pro  Gly  Gly  Ser  Val  Asp  Ile  Val  Ala  Met  Asp  Glu  Gly
385                      390                      395                      400

TCA  GAA  GCA  TCC  TCC  TGC  TCA  TCT  GCT  TTG  GCC  TCG  AAG  CCC  AGC  CCA      1248
Ser  Glu  Ala  Ser  Ser  Cys  Ser  Ser  Ala  Leu  Ala  Ser  Lys  Pro  Ser  Pro
                    405                      410                      415

GAG  GGA  GCC  TCT  GCT  GCC  AGC  TTT  GAG  TAC  ACT  ATC  CTG  GAC  CCC  AGC      1296
Glu  Gly  Ala  Ser  Ala  Ala  Ser  Phe  Glu  Tyr  Thr  Ile  Leu  Asp  Pro  Ser
```

```
                         420                           425                           430
     TCC  CAG  CTC  TTG  CGT  CCA  TGG  ACA  CTG  TGC  CCT  GAG  CTG  CCC  CCT  ACC              1344
     Ser  Gln  Leu  Leu  Arg  Pro  Trp  Thr  Leu  Cys  Pro  Glu  Leu  Pro  Pro  Thr
          435                      440                           445

CCA  CCC  CAC  CTA  AAG  TAC  CTG  TAC  CTT  GTG  GTA  TCT  GAC  TCT  GGC  ATC              1392
     Pro  Pro  His  Leu  Lys  Tyr  Leu  Tyr  Leu  Val  Val  Ser  Asp  Ser  Gly  Ile
          450                      455                           460

TCA  ACT  GAC  TAC  AGC  TCA  GGG  GAC  TCC  CAG  GGA  GCC  CAA  GGG  GGC  TTA              1440
     Ser  Thr  Asp  Tyr  Ser  Ser  Gly  Asp  Ser  Gln  Gly  Ala  Gln  Gly  Gly  Leu
     465                           470                 475                           480

TCC  GAT  GGC  CCC  TAC  TCC  AAC  CCT  TAT  GAG  AAC  AGC  CTT  ATC  CCA  GCC              1488
     Ser  Asp  Gly  Pro  Tyr  Ser  Asn  Pro  Tyr  Glu  Asn  Ser  Leu  Ile  Pro  Ala
                    485                      490                           495

GCT  GAG  CCT  CTG  CCC  CCC  AGC  TAT  GTG  GCT  TGC  TCT  TAG                             1527
     Ala  Glu  Pro  Leu  Pro  Pro  Ser  Tyr  Val  Ala  Cys  Ser
                    500                      505
```

( 2 ) INFORMATION FOR SEQ ID NO:5:

( i ) SEQUENCE CHARACTERISTICS:
        ( A ) LENGTH: 508 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met  Asp  His  Leu  Gly  Ala  Ser  Leu  Trp  Pro  Gln  Val  Gly  Ser  Leu  Cys
 1                  5                        10                       15

Leu  Leu  Leu  Ala  Gly  Ala  Ala  Trp  Ala  Pro  Pro  Asn  Leu  Pro  Asp
               20                  25                       30

Pro  Lys  Phe  Glu  Ser  Lys  Ala  Ala  Leu  Leu  Ala  Ala  Arg  Gly  Pro  Glu
          35                       40                       45

Glu  Leu  Leu  Cys  Phe  Thr  Glu  Arg  Leu  Glu  Asp  Leu  Val  Cys  Phe  Trp
     50                       55                  60

Glu  Glu  Ala  Ala  Ser  Ala  Gly  Val  Gly  Pro  Gly  Asn  Tyr  Ser  Phe  Ser
65                       70                       75                       80

Tyr  Gln  Leu  Glu  Asp  Glu  Pro  Trp  Lys  Leu  Cys  Arg  Leu  His  Gln  Ala
               85                       90                       95

Pro  Thr  Ala  Arg  Gly  Ala  Val  Arg  Phe  Trp  Cys  Ser  Leu  Pro  Thr  Ala
               100                      105                      110

Asp  Thr  Ser  Ser  Phe  Val  Pro  Leu  Glu  Leu  Arg  Val  Thr  Ala  Ala  Ser
               115                      120                      125

Gly  Ala  Pro  Arg  Tyr  His  Arg  Val  Ile  His  Ile  Asn  Glu  Val  Val  Leu
     130                      135                      140

Leu  Asp  Ala  Pro  Val  Gly  Leu  Val  Ala  Arg  Leu  Ala  Asp  Glu  Ser  Gly
145                      150                      155                      160

His  Val  Val  Leu  Arg  Trp  Leu  Pro  Pro  Glu  Thr  Pro  Met  Thr  Ser
                    165                      170                      175

His  Ile  Arg  Tyr  Glu  Val  Asp  Val  Ser  Ala  Gly  Asn  Gly  Ala  Gly  Ser
                    180                      185                      190

Val  Gln  Arg  Val  Glu  Ile  Leu  Glu  Gly  Arg  Thr  Glu  Cys  Val  Leu  Ser
          195                      200                      205

Asn  Leu  Arg  Gly  Arg  Thr  Arg  Tyr  Thr  Phe  Ala  Val  Leu  Ala  Arg  Met
     210                      215                      220

Ala  Glu  Pro  Ser  Phe  Gly  Gly  Phe  Trp  Ser  Ala  Trp  Ser  Glu  Pro  Val
225                      230                      235                      240

Ser  Leu  Leu  Thr  Pro  Ser  Asp  Leu  Asp  Pro  Leu  Ile  Leu  Thr  Leu  Ser
```

-continued

|  |  |  |  |  |  |  |  | 245 |  |  |  | 250 |  |  |  | 255 |  |
|---|---|---|---|---|---|---|---|---|---|---|---|---|---|---|---|---|---|
| Leu | Ile | Leu | Val 260 | Val | Ile | Leu | Val | Leu 265 | Leu | Thr | Val | Leu | Ala 270 | Leu | Leu |
| Ser | His | Arg 275 | Arg | Ala | Leu | Lys | Gln 280 | Lys | Ile | Trp | Pro | Gly 285 | Ile | Pro | Ser |
| Pro | Glu 290 | Ser | Glu | Phe | Glu | Gly 295 | Leu | Phe | Thr | Thr | His 300 | Lys | Gly | Asn | Phe |
| Gln 305 | Leu | Trp | Leu | Tyr | Gln 310 | Asn | Asp | Gly | Cys | Leu 315 | Trp | Trp | Ser | Pro | Cys 320 |
| Thr | Pro | Phe | Thr | Glu 325 | Asp | Pro | Pro | Ala | Ser 330 | Leu | Glu | Val | Leu | Ser 335 | Glu |
| Arg | Cys | Trp | Gly 340 | Thr | Met | Gln | Ala | Val 345 | Glu | Pro | Gly | Thr | Asp 350 | Asp | Glu |
| Gly | Pro | Leu 355 | Leu | Glu | Pro | Val | Gly 360 | Ser | Glu | His | Ala | Gln 365 | Asp | Thr | Tyr |
| Leu | Val 370 | Leu | Asp | Lys | Trp | Leu 375 | Leu | Pro | Arg | Asn | Pro 380 | Pro | Ser | Glu | Asp |
| Leu 385 | Pro | Gly | Pro | Gly | Gly 390 | Ser | Val | Asp | Ile | Val 395 | Ala | Met | Asp | Glu | Gly 400 |
| Ser | Glu | Ala | Ser | Ser 405 | Cys | Ser | Ser | Ala | Leu 410 | Ala | Ser | Lys | Pro | Ser 415 | Pro |
| Glu | Gly | Ala | Ser 420 | Ala | Ala | Ser | Phe | Glu 425 | Tyr | Thr | Ile | Leu | Asp 430 | Pro | Ser |
| Ser | Gln | Leu 435 | Leu | Arg | Pro | Trp | Thr 440 | Leu | Cys | Pro | Glu | Leu 445 | Pro | Pro | Thr |
| Pro | Pro 450 | His | Leu | Lys | Tyr | Leu 455 | Tyr | Leu | Val | Val | Ser 460 | Asp | Ser | Gly | Ile |
| Ser 465 | Thr | Asp | Tyr | Ser | Ser 470 | Gly | Asp | Ser | Gln | Gly 475 | Ala | Gln | Gly | Gly | Leu 480 |
| Ser | Asp | Gly | Pro | Tyr 485 | Ser | Asn | Pro | Tyr | Glu 490 | Asn | Ser | Leu | Ile | Pro 495 | Ala |
| Ala | Glu | Pro | Leu 500 | Pro | Pro | Ser | Tyr | Val 505 | Ala | Cys | Ser |  |  |  |  |

EXPRESSION OF A CLEAVABLE FUSION PROTEIN COMPRISING A SOLUBLE HUMAN ERYTHROPOIETIN RECEPTOR PROTEIN FRAGMENT

This is a continuation of application Ser. No. 08/499,643, filed Jul. 7, 1995, now abandoned, which is in turn a continuation of application Ser. No. 08/106,815, filed Aug. 16, 1993, now abandoned.

FIELD OF THE INVENTION

This invention relates to purified human erythropoietin receptor extracellular domain polypeptide. More particularly, this invention relates to human erythropoietin receptor extracellular domain polypeptide that retains affinity for erythropoietin, to DNA sequences suitable for use in producing such a polypeptide, and to antibodies recognizing such a polypeptide.

BACKGROUND OF THE INVENTION

Erythropoietin (Epo) is a glycoprotein hormone of molecular weight 34 kilodaltons (kDa) that is produced in the mammalian kidney and liver. Epo is a key component in erythropoiesis, inducing the proliferation and differentiation of red cell progenitors. Epo activity also is associated with the activation of a number of erythroid-specific genes, including globin and carbonic anhydrase. Bondurant et al., *Mol. Cell Biol.* 5: 675–683 (1985); Koury et al., *J. Cell. Physiol.* 126: 259–265 (1986). The erythropoietin receptor (EpoR) is a member of the hematopoietic/cytokine/growth factor receptor family, which includes several other growth factor receptors, such as the interleukin (IL)-3, -4 and -6 receptors, the granulocyte macrophage colony-stimulating factor (GM-CSF) receptor as well as the prolactin and growth hormone receptors. Bazan, *Proc. Natl. Acad. Sci USA* 87: 6934–6938 (1990). Members of the cytokine receptor family contain four conserved residues and a tryptophan-serine-X-tryptophan-serine motif positioned just outside the transmembrane region. The conserved sequences are thought to be involved in protein-protein interactions. Chiba et al., *Biochim. Biophys. Res. Comm.* 184: 485–490 (1992).

EpoR cDNA has been isolated recently from mouse liver, Tojo et al., *Biochem. Biophys. Res. Comm.* 148: 443–48 (1987) and from human fetal liver. Jones et al., *Blood* 76: 31–35 (1990); Winkelmann et al., *Blood* 76: 24–30 (1990). The full length EpoR cDNA sequence is shown in the Sequence Listing as SEQ ID NO: 4. The human cDNA encodes a polypeptide chain of MW ~55 kDa and having about 508 amino acids. Genomic clones of human EpoR have been isolated and sequenced. Penny and Forget, *Genomics* 11: 974–80 (1991); Noguchi et al., *Blood* 78: 2548–2556 (1991). Analysis of the coding sequence predicts about 24 amino acid residues in a signal peptide, about 226 amino acids in an extracellular domain, about 23 amino acids in a membrane-spanning domain, and about 235 amino acids in a cytoplasmic domain. D'Andrea and Zon, *J. Clin. Invest.* 86: 681–687 (1990); Jones et al., *Blood* 76: 31–35, (1990); Penny and Forget, *Genomics* 11: 974–80 (1991). The mature human EpoR protein has about 484 amino acids. All human erythroid progenitor cells have been shown to contain Epo receptors. Binding of Epo appears to decline as erythroid progenitor cells mature, until Epo receptors are not detectable on reticulocytes. Sawada et al., *J. Clin. Invest.* 80: 357–366 (1987). Sawada et al., *J. Cell. Physiol.* 137: 337 (1988). Epo maintains the cellular viability of the erythroid progenitor cells and allows them to proceed with mitosis and differentiation. Two major erythroid progenitors responsive to Epo are the Burst-forming units-erythroid (BFU-E) and the Colony-forming units-erythroid (CFU-E). The Epo receptor number correlates very well with the response to Epo in normal BFU-E and CFU-E. Epo receptor numbers appear to decline after reaching the peak receptor number at the CFU-E stage in human and murine cells. Sawada et al., *J. Clin. Invest.* 80: 357–366 (1987); Landschulz et al., *Blood* 73: 1476–1486 (1989). The recovery of Epo receptors after removal of Epo appears to be dependent on protein synthesis, which suggests downregulation of Epo receptor by degradation, and the subsequent upregulation of receptors by the new synthesis of receptors when Epo is removed. Sawyer and Hankins, *Blood* 72: 132 (1988). Studies of Epo receptors on megakaryocytes and erythroid progenitors suggest that there is a link between the regulation of erythropoiesis and thrombopoiesis, in that stimulation of cell division by both cell types is controlled by Epo receptor numbers. Berridge et al., *Blood* 72: 970–977 (1988). Although the Epo receptor has been cloned, the precise mechanisms involved in binding of Epo to Epo receptors and the relationship to subsequent erythropoietic processes are not known.

Characterization of the Epo receptor (EpoR) has been difficult due to the extremely small quantities of EpoR that can be obtained from natural sources. Thus, the mechanism of Epo interaction with its receptor, which stimulates erythropoiesis, is still unknown. D'Andrea and Zon, *J. Clin. Invest.* 86: 681–687 (1990). Recently this mechanism has been of great interest in understanding the role of growth factors and their receptors in leukemogenesis; altered hematopoietic growth factors and their receptors may contribute to tumorigenesis and leukemogenesis. Dunbar et al., *Science* 245: 1493–1496 (1989); Li et al., *J. Virol.* 57: 534–538 (1986).

Several studies of the correlation between the Epo responsiveness of a particular cell type and the affinity of the cell type for Epo have reported discordant results. These studies have used recombinant Epo or EpoR possessing some non-native amino acid sequence from the corresponding plasmid vectors. Berridge et al., *Blood* 72: 970–977 (1988); Harris et al., *J. Biol. Chem.* 267: 15205–09 (1992). It is possible that tertiary structural changes and/or other features of these recombinant Epo or EpoR molecules have changed the characteristics of the native protein. Thus, it would be a significant advance to obtain substantially pure fragments of the Epo receptor, free of extraneous (e.g, vector) amino acid sequence. Although it could not be predicted whether or not such fragments would retain functional activity, nevertheless a purified extracellular domain fragment would be particularly useful since Epo binds to the extracellular domain of the Epo receptor.

SUMMARY OF THE INVENTION

An expression vector is disclosed, comprising a first nucleotide sequence capable of expressing a polypeptide that has a thrombin proteolytic cleavage site near the carboxyl terminus and a second nucleotide sequence consisting essentially of nucleotides 73 to 750 of a full length human erythropoietin receptor cDNA coding sequence. The Epo receptor cDNA coding sequence (SEQ ID NO.: 5) fragment is positioned 3' to (downstream of) the proteolytic cleavage site and is in the same translational reading frame as the proteolytic cleavage site. The Epo receptor cDNA coding sequence fragment is oriented to be translationally contiguous with the first polynucleotide sequence.

A purified fusion protein is disclosed, comprising a first segment consisting essentially of a polypeptide produced by an expression vector and having a thrombin proteolytic cleavage site, and a second segment consisting essentially of about amino acid 25 to about amino acid 250 of the full length human erythropoietin receptor protein (SEQ ID NO: 5). The second segment is covalently coupled to the carboxyl end of the first segment. A purified protein, consisting essentially of about amino acid 25 to about amino acid 250 of the full length human erythropoietin receptor protein sequence (SEQ ID NO: 5), may be produced by thrombin cleavage of the fusion protein.

An antibody having affinity for a purified human erythropoietin receptor polypeptide extracellular domain is disclosed. The antibody has affinity for a polypeptide comprising about amino acid 25 to about amino acid 250 of the full length human erythropoietin receptor protein sequence (SEQ ID NO: 5).

An immunoassay composition comprising a solid phase reagent and the antibody operably coupled to the solid phase reagent, is disclosed. Also disclosed is an immunoassay composition comprising a solid phase reagent and the purified protein operably coupled to the solid phase reagent.

Methods for obtaining a substantially pure human erythropoietin receptor polypeptide consisting essentially of about amino acid 25 to about amino acid 250 of the full length human erythropoietin receptor protein (SEQ ID NO: 5) are disclosed. The substantially pure human erythropoietin receptor polypeptide retains the ability to bind specifically to erythropoietin. The methods include treating the fusion protein with thrombin under conditions allowing cleavage of the polypeptide from the fusion protein, to form a digest mixture; adding the digest mixture to a solid phase reagent having erythropoietin coupled thereto, under conditions allowing binding of the polypeptide with the solid phase reagent, to form a polypeptide-solid phase composition; washing the polypeptide-solid phase composition to remove unbound material; and eluting the substantially pure human erythropoietin receptor polypeptide from the polypeptide-solid phase composition.

BRIEF DESCRIPTION OF THE FIGURES

FIG. 1 also depicts the recombinant fusion protein, EpoRex-th, that is expressed from pJYL26.

DETAILED DESCRIPTION OF THE INVENTION

Figure 1:
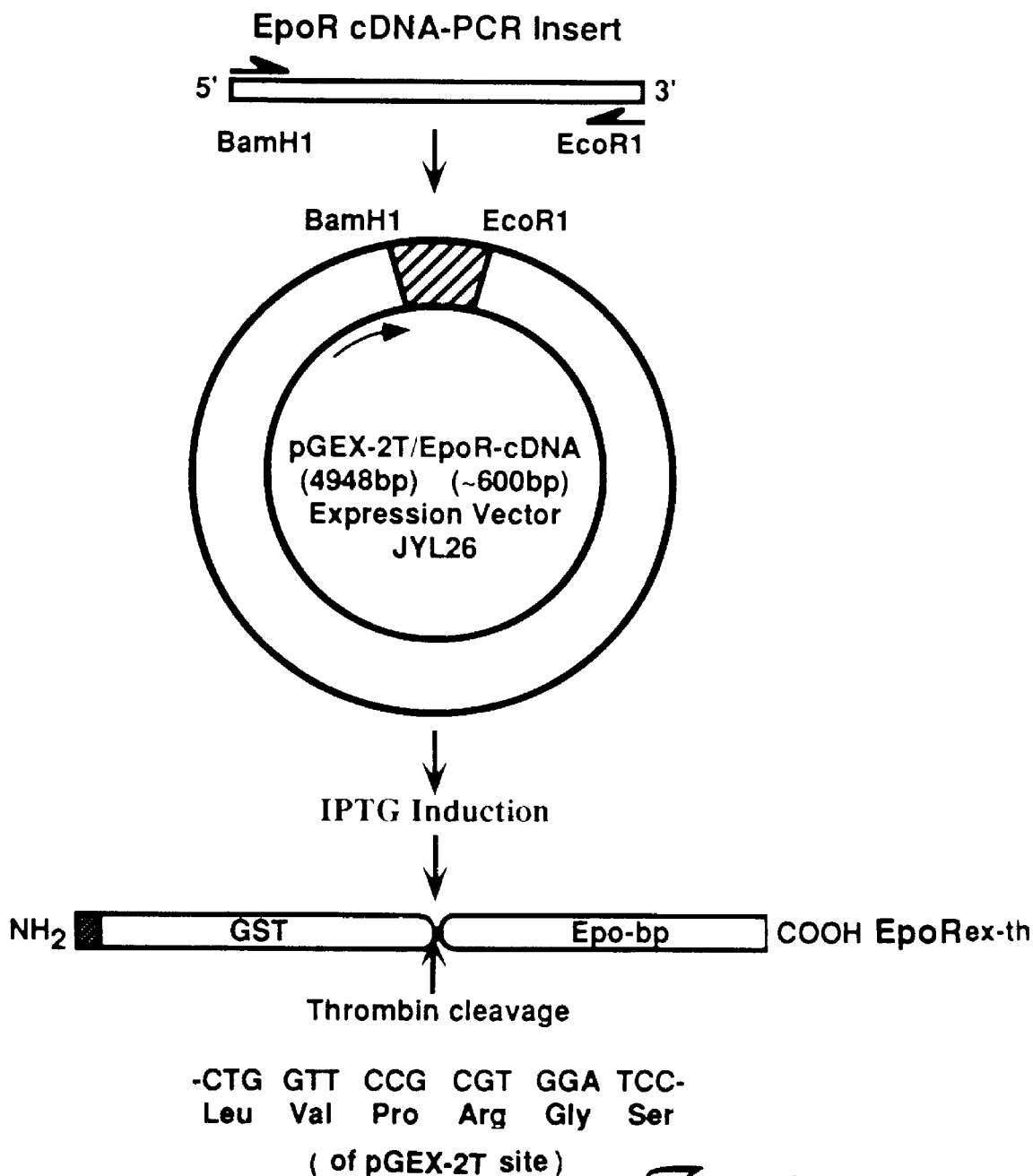
FIG. 1 is a diagrammatic representation of pJYL26, a plasmid having about 678 bp of the 5' coding sequence of human erythropoietin receptor cDNA inserted into the expression vector pGEX-2T.

Despite the availability of recombinant human Epo and full-length human Epo receptor cDNA clones, little is known about the interaction of Epo and Epo receptor, or the signal transducing mechanisms involved in proliferation and differentiation of erythroid progenitor cells.

Plasmid expression vectors permit expression of a protein from cloned coding sequences that have been inserted into the vector. Expression vectors generally have a selectable marker and a replication origin for selection and maintenance of the vector in a host cell, as well as inducible regulatory elements for inducing high level expression of a polypeptide suitable for fusing to an inserted gene. It is preferred that convenient restriction sites be engineered into the vector downstream from a proteolytic cleavage site sequence. A preferred polypeptide to be fused to the Epo coding sequence fragment is glutathione S-transferase, possessing a thrombin proteolytic cleavage site at the carboxyl terminus.

An expression vector for the invention disclosed herein expresses the EpoR extracellular domain as part of a fusion protein that can subsequently be cleaved to yield purified EpoR extracellular domain. The coding sequence for the EpoR extracellular domain may be engineered in any manner suitable for inserting the sequence in the appropriate reading frame in the expression vector. For example, a pair of polymerase chain reaction (PCR) primers may be synthesized, such that the first primer corresponds to the coding sequence at the 5' end of the extracellular domain and the second primer is complementary to the coding sequence of the 3' end of the extracellular domain. The primers preferably have convenient restriction enzyme sites flanking the portions of the primers corresponding to the ends of the desired target sequences. The primers are used to amplify the EpoR extracellular domain from a full length human EpoR cDNA template. The resulting PCR product is then cloned into an expression vector. It is preferable to synthesize PCR primers having different restriction sites at each end, rather than the same restriction site. The presence of different restriction sites at each end of the PCR product facilitates the insertion of the human EpoR coding sequence fragment in the sense orientation.

High level expression of a fusion protein having human erythropoietin receptor extracellular domain as part of the fusion protein is achieved by inducing expression from the recombinant plasmid expression vector in a host cell culture. A fusion protein is hereinafter referred to as EpoRex-th and a purified human erythropoietin receptor extracellular domain hereinafter is referred to as Epo-bp. A cell protein extract is preferably prepared from an expressing *E. coli* culture in any suitable manner. EpoRex-th may be purifed from the extract as desired. For example, the extract may be passed over a column having the ability to bind the portion of the fusion protein upstream of the Epo-bp coding sequence. The fusion protein will bind to the column, while other proteins in the extract are eluted in column washes with a buffer that allows binding of fusion protein to the column matrix. EpoRex-th can be subsequently eluted in high purity by changing the buffer conditions.

Purification of Epo-bp may be accomplished by cleaving purified EpoRex-th using an appropriate cleavage method. For example, the cleavage site between the upstream polypeptide and Epo-bp may be sensitive to cyanogen bromide or, alternatively, may be sensitive to site-specific protease cleavage. In a preferred embodiment, a thrombin proteolytic cleavage site is engineered into the upstream polypeptide, but 5' to the convenient restriction cloning sites positioned at the carboxyl terminus of the upstream polypeptide coding sequence.

The cleaved Epo-bp polypeptide segment may be separated from the upstream polypeptide segment by purification techniques such as size exclusion chromatography, isoelectric focusing, or affinity chromatography. Furthermore, more than one purification technique may be used, if desired, to achieve the appropriate degree of purification. A preferred purification technique is affinity chromatography. For example, a protease-treated fusion protein mixture may be applied to a column having agarose beads coupled to Epo. The cleaved Epo-bp segment will bind to the Epo-agarose, while the upstream polypeptide segment will pass through the column. Epo-bp may then be eluted by lowering the pH of the liquid phase.

In an embodiment of the invention, the coding sequence for amino acids 25 through 250 of human EpoR (hEpoR) is cloned into pGEX-2T (Pharmacia, Mechanicsburg, Pa.). pGEX-2T has an IPTG inducible promoter operably linked to a coding sequence for glutathione S-transferase (GST). The 3' end of the GST coding sequence has a thrombin proteolytic cleavage site in the correct reading frame, as well as convenient cloning sites for inserting a coding sequence to be covalently coupled to GST.

A PCR product having amino acids 25 through 250 of hEpoR is made from a suitable DNA template, for example a full-length human EpoR cDNA. A PCR primer is sythesized having the 5' end of the extracellular domain coding sequence as well as a BamH1 site, and a PCR primer is synthesized having sequence complementary to the 3' end of the extracellular domain coding sequence as well as an EcoR1 site. The BamH1 site in pGEX-2T is positioned 5' to the EcoR1 site relative to the GST coding sequence. The PCR product is cloned into pGEX-2T, and a transformed *E. coli* colony having a plasmid of the expected size is identified.

A fusion protein having an amino terminal GST segment and a carboxy terminal EpoR extracellular domain segment is expressed in transformed *E. coli* by inducing transcription with IPTG. IPTG derepresses the lac promoter positioned upstream of the fusion protein coding sequence. After allowing expression for a period of time sufficient to accumulate an amount of the fusion protein, cells are lysed and a crude extract is made in any suitable manner. The crude extract mixture has the fusion protein in addition to many other cellular proteins. The fusion protein, EpoRex-th, may be purified from the extract as desired.

In a preferred embodiment, EpoRex-th is passed over a column having agarose beads coupled to glutathione (GSH). GSH is a substrate for GST, and the GST segment of EpoRex-th will bind to the immobilized GSH with high affinity. Thus, the fusion protein becomes bound to the column, while virtually all other proteins in the extract will not bind. After washing, EpoRex-th may be eluted from the column by adding reduced GSH to the liquid phase.

In an embodiment of the invention, purified human erythropoietin receptor extracellular domain polypeptide may be made by digesting EpoRex-th with thrombin. The resulting digested mixture of GST and Epo-bp may then be applied to an Epo affinity column. The Epo-bp binds to its ligand, Epo, whereas GST passes through the column. Epo-bp may be eluted in purified form through use of an appropriate elution buffer, for example 0.1M glycine, pH 3.0.

Antibodies to human erythropoietin receptor extracellular domain can be made by presentation of a purified preparation of such a polypeptide to the immune system of an animal. For example, purified Epo-bp may be injected subcutaneously, intramuscularly or intraperitoneally into animals such as rats, mice, rabbits, or sheep. Booster injections can be given at intervals, if desired. Circulating antibodies against Epo-bp are made by the immune system of the injected animal, and these antibodies can be collected from the blood, preferably from the serum. Anti-Epo-bp serum can be used to detect Epo-bp in various assay formats, such as Western blots, ELISA assays and the like. Epo-bp to be detected may be from, for example, a purified preparation of Epo-bp, a bacterial or eukaryotic cell extract, a eukaryotic cell from an in vitro cell culture, a serum sample, or even a tissue or cell biopsy taken from an individual. Anti-Epo-bp antibodies are expected to recognize the extracellular domain of intact human EpoR as well as Epo-bp. Monoclonal antibodies directed against Epo-bp can be made by methods known in the art. D'Andrea et al., *Blood* 75: 874–80 (1990); Goldwasser et al., U.S. Pat. No. 4,558,005; Harlow and Lane, *Antibodies—Lab Manual,* Cold Spring Harbor Laboratory, 1988.

Antibodies directed against Epo-bp preferably have a specific binding affinity for the EpoR extracellular domain. For example, serum from an animal injected with purified Epo-bp should provide detectable binding to Epo-bp in Western blots when 10 µg of purified Epo-bp are electrophoresed in a polyacrylamide gel and exposed to a 1:2000 dilution of the anti-Epo-bp serum.

The purified extracellular domain of EpoR disclosed herein is the first such pure human Epo receptor fragment (i.e., free of non-human or non-Epo receptor amino acid sequence) to be obtained. The experiments disclosed herein demonstrate that such a fragment retains the ability to specifically bind human Epo. The proteins and antibodies disclosed herein are useful for understanding the mechanisms of Epo-Epo receptor interaction. The purified Epo-bp of the present invention is also useful for investigating the structure of the Epo receptor and for identifying factors involved in regulating differentiation and proliferation mechanisms in erythroid progenitor cells. Moreover, the invention disclosed herein is useful for identifying and quantitating Epo and Epo receptor, as well as in understanding hematopoietic malignancy and certain cardiovascular system disorders. That is, increased/decreased hematocrit and/or hemoglobin levels may affect blood pressure and cause other circulatory problems.

The invention will be further understood with reference to the following illustrative embodiments, which are purely exemplary, and should not be taken as limiting the true scope of the present invention as described in the claims.

EXAMPLE 1

Materials

Glutathione (GSH)-agarose, pGEX-2T expression vector and Sephadex G-50 were purchased from Pharmacia (Mechanicsburg, Pa.). PCR reagents were from Perkin-Elmer Cetus (Norwalk, Conn.) and Affigel 15 was from BioRad (Richmond, Calif.). Bacteriophage T4 DNA ligase, restriction enzymes and isopropylthio-β-D-galactoside (IPTG) were purchased from BRL Gibco (Gaithersburg, Md.). Geneclean II was from Bio 101, La Jolla, Calif. Nitrocellulose was from Schleicher & Schuell Co. (Keene, N.H.). Chemiluminescence (ECL) reagents and $^{125}$I-Epo were from Amersham (Arlington Heights, Ill.) and unlabeled Epo was a gift of Chugai-Upjohn (Rosemont, Ill.). Phenylmethylsulfonylfluoride (PMSF), diisopropylfluorophosphate (DFP), thrombin, trypsin and Triton X-100, were from Sigma Chemical Company (St. Louis, Mo.). Biotinylated rabbit anti-sheep antibodies and avidin-horseradish peroxidase were from Pierce Co. (Rockford, Ill.). LAP37, a full-length human erythropoietin receptor (EpoR) cDNA preparation, was provided by Dr. Bernard G. Forget, Yale University, New Haven, Conn. All other chemicals were of reagent grade.

EXAMPLE 2

Construction of EpoR cDNA Recombinant Vector

A recombinant plasmid expression vector, pJYL26, was constructed from a PCR product having the human Epo receptor extracellular domain coding sequence and from the plasmid vector pGEX-2T. The construction of this plasmid is explained below.

PCR amplification was carried out using a full-length human EpoR cDNA, LAP37, as a template. The 5'-sense primer was 5'-TTGGATCCGCGCCCCCGCCTAAC- 3' (SEQ ID NO: 1). This primer has a BamH1 linker sequence at the 5' end, followed by the coding sequence for amino acids 25 through 29 of the full length human EpoR protein. The 3'-antisense primer was 5'-TGAATTCGGGGTCCAGGTCGCT-3' (SEQ ID NO: 2). This primer has an EcoR1 linker followed by sequence complementary to the coding sequence for amino acids 226 through 222 of full length EpoR. Using a Perkin Elmer-Cetus PCR kit, PCR was carried out with 0.1 µg of LAP37 cDNA, 20 pM of each primer, 1.25 mM dNTP mixture (dGTP, dCTP, dTTP and dATP), 0.5 µl of Taq polymerase, and 10 x buffer supplied in the PCR kit. Amplification was carried out by a PTC-100 Programmable Thermal Controller, (M. J. Research, Inc. Watertown, Mass.), with denaturation at 94° C. for 1 min, annealing at 55° C. for 1 min and extension at 72° C. for 1½ min, repeated for 25 cycles.

The sizes of the PCR product (~600 bp) and pGEX-2T (~4.9 kb) were verified on 1% Seakem and 2% Nusieve agarose (FMC Bioproducts, Rockland, Me.) gels running in 1 x TA buffer (50 x TA in 1 liter volume containing 242 g Tris-base and 57.1 ml acetic acid), with a Hae II standard. Both the PCR product and pGEX-2T were purified from gel slices by the Geneclean II method as described by the manufacturer (Bio 101, La Jolla, Calif.). Concentrations of the PCR product and pGEX-2T were estimated by absorbance readings at OD260. Both DNAs were then digested with BamH1 and EcoR1 for 4 hours at 37° C. before ligation. The digested products were analyzed on 1% Seakem and 2% Nusieve agarose gels. Both the PCR product and pGEX-2T fragments were cut from the gel and purified again by the Geneclean II method.

The ligation was done in a mixture having 1 µg/µl each of PCR product and pGEX-2T. The mixture was incubated at 45° C. for 5 minutes and chilled to 0° C. Then, in a 10 µl final volume, 1 µl each of 10 x bacteriophage T4 DNA buffer and 10 x bacteriophage DNA ligase, and 10 mM ATP were added. The whole mixture was then incubated at 16° C. in a circulating water bath overnight. Productive ligation was verified by electrophoresis in a 1% agarose gel in 1 x TA buffer running at 100 volts with lanes containing size standards, pGEX-2T, PCR product, and the ligated product (PCR product+pGEX-2T). The ligated product was verified to be ~5.5 kb. An aliquot of ligation mixture was then transformed into E. coli strain JM109 (20 µg ligation mixture/200 µl JM109). For the transformation, the E. coli mixture was incubated on ice for 30 minutes after mixing gently by inverting, and incubated at 42° C. exactly 90 seconds. Then the mixture was chilled on ice for 1–2 minutes and 500 µl LB medium (for 1 liter, 10 g bacto-tryptone, 5 g bacto-yeast and 10 g NaCl , pH 7.5, autoclave) was added. After incubating at 37° C. for 45 minutes, the LB mixtures were spread on LB/Amp agar petri plates in amounts of 50, 75, 125, 150, and 300 ml of LB mixture. Agar petri plates were prepared with 20–30 ml of LB/Amp medium, containing 15 g agar/liter LB (autoclaved) and 100 µg/liter ampicillin. Control LB/Amp plates were made with intact pGEX-2T, digested pGEX-2T and PCR product only. The plates were kept on the bench top to absorb liquid for a few hours and inverted plates were incubated at 37° C. for 24 hours. Grown colonies were seeded on gridded plates, which were incubated again at 37° C. for 24 hours, while another set of all colonies was grown in 5 ml each of the LB/Amp medium overnight.

The DNA was extracted from each colony by the miniprep method. Each colony was cultured overnight with 5 ml LB/Amp medium (2 µl/ml of 50 µg/ml Amp stock) in a loosely capped 15-ml plastic tube in a vigorously shaking 37° C. incubator. The following day, 1.5 ml of each culture was pelleted in a microfuge for 3 minutes at 4° C. at 14,000 x g, and resuspended in 93 µl STET plus 17 µl of lysozyme stock (STET: 5% sucrose +5% Triton X-100+50 mM Tris, pH 8.0+50 mM EDTA, pH 8.0, stored at 4° C.; lysozyme stock: 5 mg/ml, stored in a freezer). The resuspended mixture was then incubated for 10 minutes at room temperature and boiled for 2 minutes before spinning in a microfuge at 4° C. for 15 minutes at 14,000 x g. The pellet was removed with a sterile tooth pick, 2 µl of RNAse (100 mg/ml) was added to the supernatant, followed by incubation at 37° C. for 30 minutes. After incubation, 110 µl of ice-cold isopropanol was added and the mixture was inverted 4 times before pelleting at 14,000 x g, 4° C. for 15 minute. The pellet (DNA) was then washed with ~1 ml of 70% ethanol to remove residual STET and other contaminants, and the pellet centrifuged again at 14,000 x g, 4° C. for 15 minutes. The pellet was then air dried for 1–2 hours and resuspended in 25 µl of sterile dH$_2$O.

The extracted DNAs were verified on a 0.8% agarose gel in TA buffer, running at 100 volts until the front dye line migrated ⅔ of the length of the gel. The gel was stained with ethidium bromide (0.5 µg/ml) at room temperature for 15 minutes on a gentle shaker and destained with dH$_2$O for 15 minutes. DNA bands were examined under UV light. Cultures having DNA of the expected size were examined in 1% agarose gels running in TA buffer after EcoR1 and/or EcoR1 plus BamH1 digestion. The EcoR1 and BamH1 digestion was done by incubating the sample mixture at 37° C. water bath for 2 hours with the mixture of 1 µg of EcoR1 or BamH1 per 2 µg of DNA in 1 µl/10 µl sample volume of 10 x reaction buffer provided in the restriction enzyme kit. One colony having a plasmid of about ~5.5 kb in size was selected after examining both EcoR1 and EcoR1 plus BamH1 digested DNA sizes in 1% agarose gels. The plasmid in this colony was named pJYL26. A diagram of pJYL26 is shown in the upper part of FIG. 1.

EXAMPLE 3

Purification of EpoRex-th Fusion Protein

This example teaches the production and purification of a fusion protein having two segments. The first segment is a polypeptide, GST, with a thrombin cleavage site at the carboxyl terminus. The second segment, fused to the first segment at the thrombin cleavage site, is the extracellular domain of human Epo receptor. The fusion protein EpoRex-th, containing GST and Epo-bp, is purified by GSH-agarose affinity chromatography.

Transformed E. coli containing the recombinant vector pJYL26 were grown overnight at 37° C. with vigorous shaking in 400 ml of LB medium with 100 µg/ml of ampicillin. The following day, the culture was diluted in 4 liters of fresh LB/Amp media and incubated for another 90 min before adding 1 mM isopropylthio-β-D-galactoside (IPTG). After 4 hours of IPTG induction, the cells were pelleted at 3,000 x g at 4° C. for 15 min and resuspended in 160 ml of lysis buffer, containing 50 mM sodium phosphate, pH 7.4, 10 mM β-mercaptoethanol (βME), 10 mM EDTA, pH 8.0, 1 mM PMSF and 1 mM DFP. 160 mg of solid lysozyme was then added. Using a 60 cc syringe, the lysed cell suspension was homogenized by passing through 18, 21 and 23 gauge needles three times, and incubated on ice 30 min. After dry ice/methanol freeze thaw at 37° C. for 3 times and mild sonication, 1% of Triton X-100 was added. The supernatant was collected by centrifugation 15 x kg at 4° C. for 15 min.

Figure 2A:
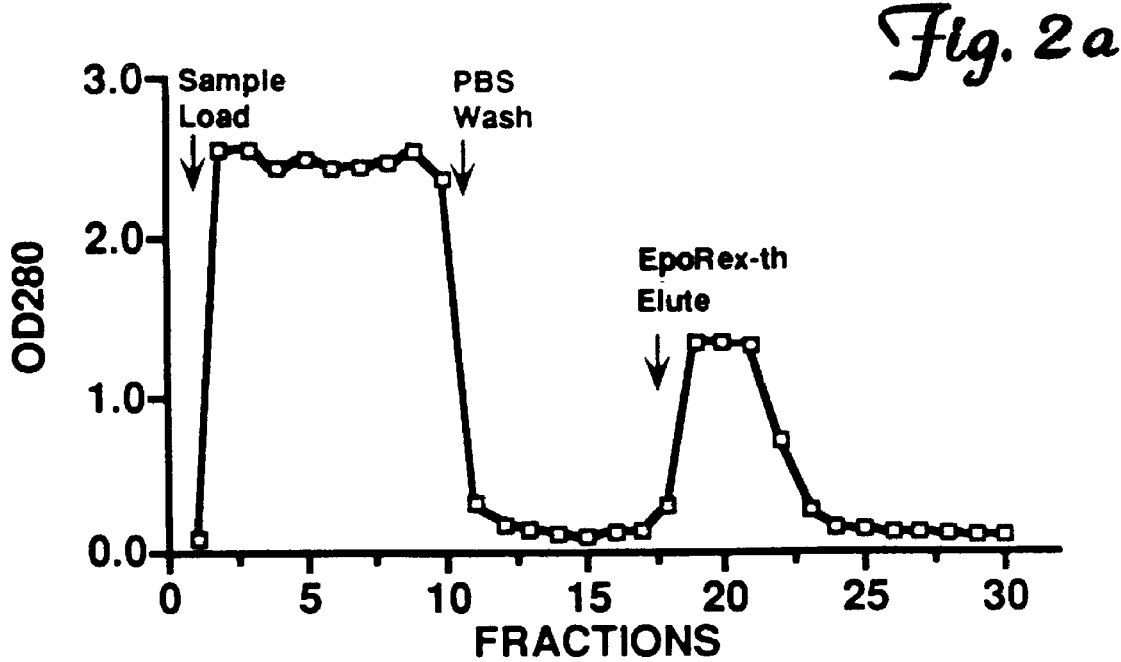
FIG. 2a shows the absorbance at 280 nanometers ($A_{280}$) of fractions collected from purification of an *E. coli* cell extract, expressing EpoRex-th, on a glutathione affinity column.
Figure 2B:
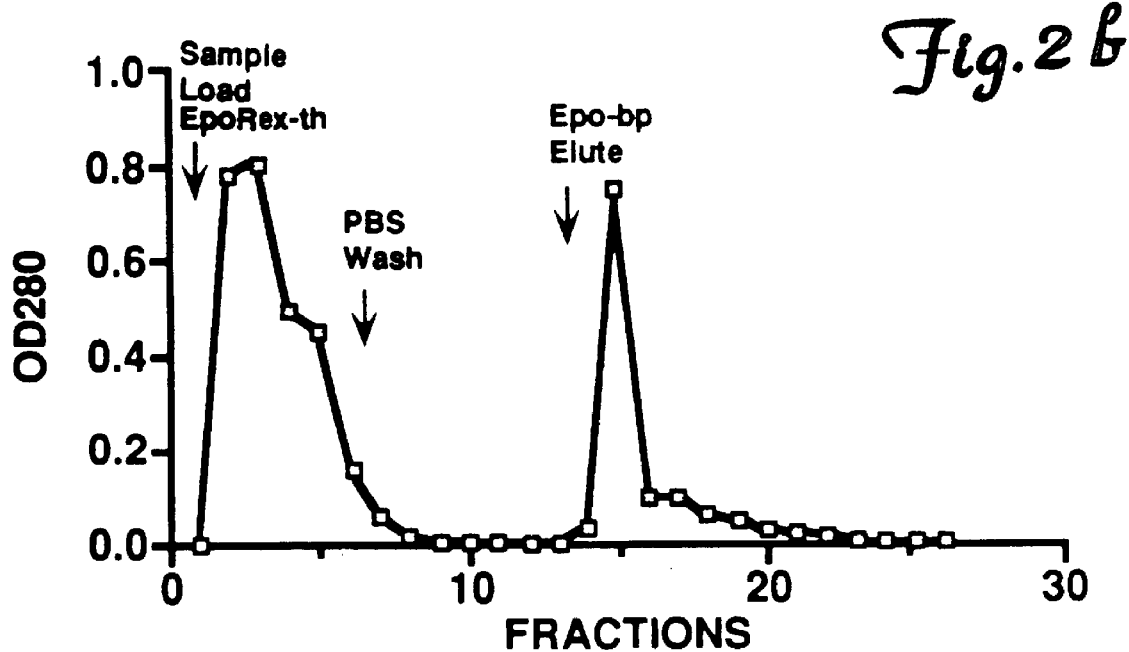
FIG. 2b shows the $A_{280}$ of fractions containing Epo-bp collected as a result of erythiopoietin affinity chromatography of thrombin treated EpoRex-th.

A GSH-agarose column was prepared by washing swollen GSH-agarose beads 3 times with 10 bed volumes of phosphate-buffered saline (PBS: 16 mM $Na_2HPO_4$, 4 mM $NaH_2PO_4$, pH 7.4 in excess salt of 3M NaCl) to remove preservatives and elutable dextran from the agarose. The column was then equilibrated with 5 bed volumes of isotonic PBS. The IPTG induced extract was applied to the column and the column was washed twice with 5 bed volumes of PBS, which elutes all proteins with no affinity for GSH-agarose. EpoRex-th was then eluted by adding 5 bed volumes of elution buffer, containing 5 mM reduced GSH in 50 mM Tris-HCl, pH 8.0. Fractions of 1.0 ml were collected and the $A_{280}$ was determined for each fraction. FIG. 2a shows the $A_{280}$ data. Fractions 18–23 were subsequently shown to have the EpoRex-th protein. These fractions were pooled. From a four-liter cell culture preparation, an average of 2 mg of EpoRex-th was extracted.

EXAMPLE 4

Purification of Epo-bp

EpoRex-th contains a thrombin-specific proteolytic cleavage site, as diagrammed in the lower half of FIG. 1. Thrombin cleaves specifically at the sequence -CTG GTT CCG CGT GGA TCC- (SEQ ID NO: 3), which codes for the amino acids Leu Val Pro Arg Gly Ser, as shown in FIG. 1. Smith and Johnson, *Gene* 67: 31–40 (1988). Thrombin was incubated with EpoRex-th to cleave the GST segment from the Epo-bp segment and the two segments were purified by Epo-agarose affinity, as described below.

Figure 3:
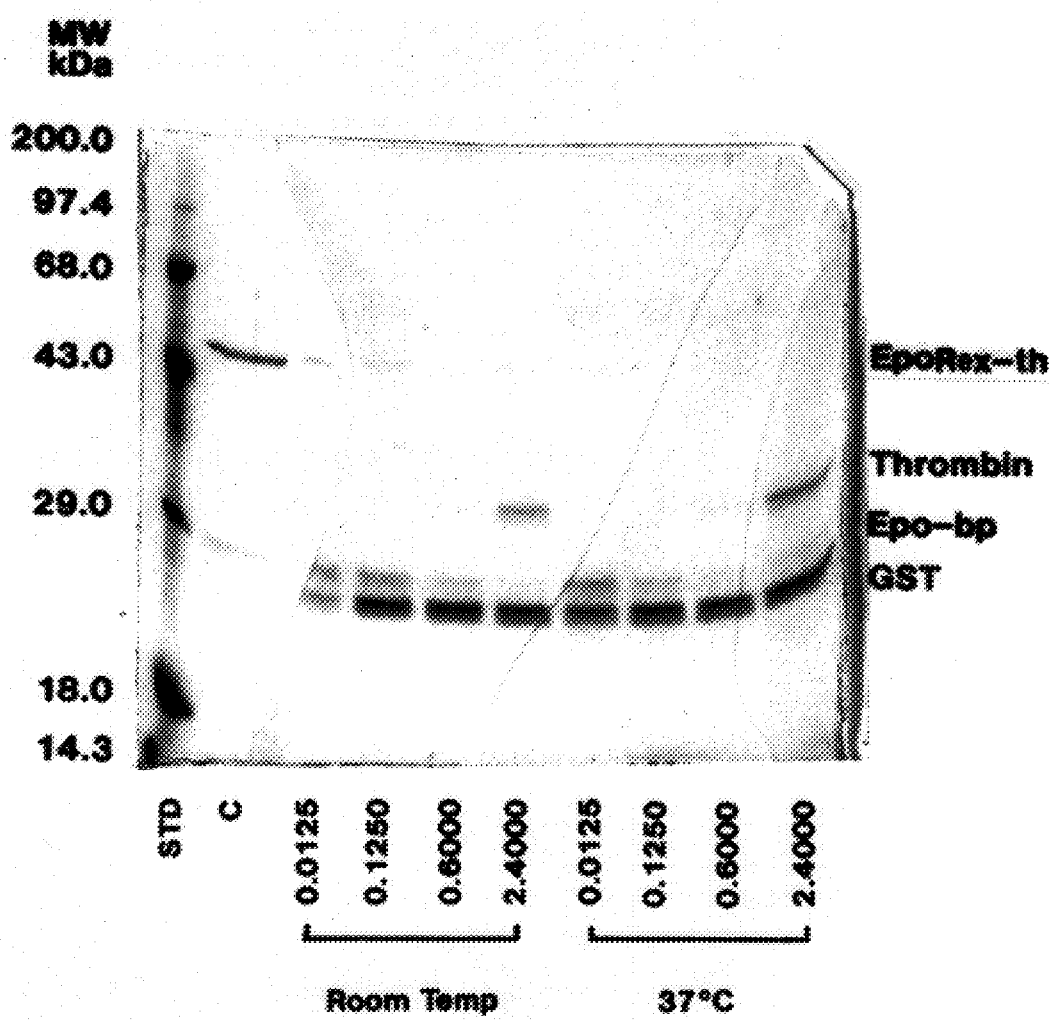
FIG. 3 is a photograph of a Coomassie blue stained polyacrylamide gel, showing the cleavage of EpoRex-th by thrombin.

Various thrombin concentrations were tested in order to find the most effective range of thrombin cleavage. Purified EpoRex-th was incubated with 0.0125, 0.125, 0.6 or 2.4 μg of thrombin per 60 μg EpoRex-th at room temperature or 37° C. for 1 hour in PBS buffer, pH 7.4. The results were analyzed by polyacrylamide gel (12.5%) electrophoresis. After staining with Coomassie blue, bands could be seen corresponding to the fusion protein EpoRex-th (55 kDa), Epo-bp (29 kDa) and GST (26 kDa). The 0.6 μg concentration was selected for complete digestion of EpoRex-th. The results are presented in FIGS. 3.

For thrombin cleavage, 60 μg of EpoRex-th was incubated at room temperature for 1 hr with 0.6 μg thrombin. The mixture was applied to an erythropoietin - agarose column in Tris buffered saline (TBS) or PBS. Epo-bp was eluted with 0.1M glycine buffer, pH 3.0. Fractions of 0.5 ml were collected into tubes, containing 0.5 ml of 2M Tris-HCl, pH 7.5. Epo-bp peak fractions 14–19 were pooled and then dialyzed overnight in TBS or PBS at 4° C. for further experiments. Approximately 200 μg Epo-bp was extracted, starting from a four-liter cell culture preparation.

The Epo-agarose column was prepared from Epo-agarose beads. The Epo-agarose beads were prepared by overnight dialysis of Epo (0.5 mg/ml) in 0.1M 3 (N-morpholino)-propanesulfonic acid (MOPS) at 4° C. Epo was linked to Affigel 15 beads by admixing 1 ml of the dialyzed Epo-solution and 2 ml of washed Affigel 15, and incubated at room temperature for 2 hours on a rotating shaker. The supernatant was removed after microcentrifuging at 2000 x g for 30 sec. The packed Epo-agarose beads were washed 3 times in TBS or PBS at 4° C. and stored until ready to use. After collecting desired protein fractions, Epo-agarose beads may be washed extensively with TBS or PBS and stored at 4° C. for reuse.

EXAMPLE 5

Production of Antibodies to Epo-bp

This example teaches the production of antibodies directed against purified Epo-bp. Purified Epo-bp is electrophoresed in a 12.5% SDS-PAGE gel and the Epo-bp protein band is resuspended in PBS and injected into sheep. Sheep serum having anti-Epo-bp antibody is shown to detect purified human Epo-bp when the serum is diluted 1:2000.

Epo-bp (0.5 mg), purified as described above, was mixed with 2 x treatment (Laemmli) buffer and boiled for 10 minutes. The mixture was applied to a 12.5% SDS gel and electrophoresed at 200 volts for 3–4 hours. The gel was stained with 0.125% Coomassie blue overnight, destained 1–2 hours with $dH_2O$, and the Epo-bp band cut out of the gel with a razor blade.

The Epo-bp gel slice was resuspended in 10–15 ml of PBS buffer and passed through a syringe repeatedly until the gel was crushed into small pieces forming a suspension mixture with PBS. The suspension was injected subcutaneously in adult sheep. Epo-bp was injected at a ratio of 0.5 mg Epo-bp or more per 25 kg weight of the animal. Two booster injections, with the same dose as in the initial injection, were given once every 3 weeks following initial injection. After the second booster injection, blood can be withdrawn for collection of antibodies. Injections can be given every month to maintain antibody production by the animal. Injection sites are rotated on the animal. Sambrook et al., *Molecular Cloning* 2nd Ed., Cold Spring Harbor Laboratory Press, Chapter 18, 1989.

To obtain blood from injected animals, hair at the blood sampling site was cleaned with 70% alcohol. Ear arteries or other accessible arteries were shaved over. A small amount of xylene was applied to the tip of the ear but not at the bleeding site. Blood was gently withdrawn with a butterfly and put into a glass tube having no heparin. The blood was incubated at room temperature for 1 hour to allow clotting, the clot was loosened from the tube wall with a pasteur pipet, and the tube was incubated at 4° C. overnight. The clotted blood mixture was poured into a dish and the clot removed. The unclotted remainder was returned to the glass tube and centrifuged at 3000 rpm for 10 minutes. The supernatant (serum) was applied to an Epo-bp-affinity column and antibodies binding to the column were eluted by with 0.1M glycine buffer, pH 3.0, using the same procedures as discussed above for purification of Epo-bp. The eluate was dialyzed in PBS overnight at 4° C. and stored at −70° C. in 500 μl aliquots. The Epo-bp affinity column was prepared from Epo-bp and Affigel 15 agarose beads in the same manner as the Epo-bp Affigel beads described in Example 6 below.

Solutions used in this example are prepared as follows:
Lysis Buffer II: 50 mM $NaPO_4$ (7.74 ml of 0.5M dibasic $PO_4$ plus 2.26 of 0.5M monobasic $PO_4$)+10 mM β-mercaptoethanol+10 mM EDTA, pH 8.
PBS Buffer: 0.15M NaCl+16 mM dibasic $PO_4$+6 mM monobasic $PO_4$, pH 7.4.

TBS buffer: for 1 liter, 12.5 ml of 2M Tris-HCl, pH7.4+27.5 ml of 5M NaCl.

2 x Treatment (Laemmli) buffer: 0.125M Tris-HCl, pH 6.8+4% SDS+20% glycerol+10% beta-mercaptoethanol.

Figure 4:
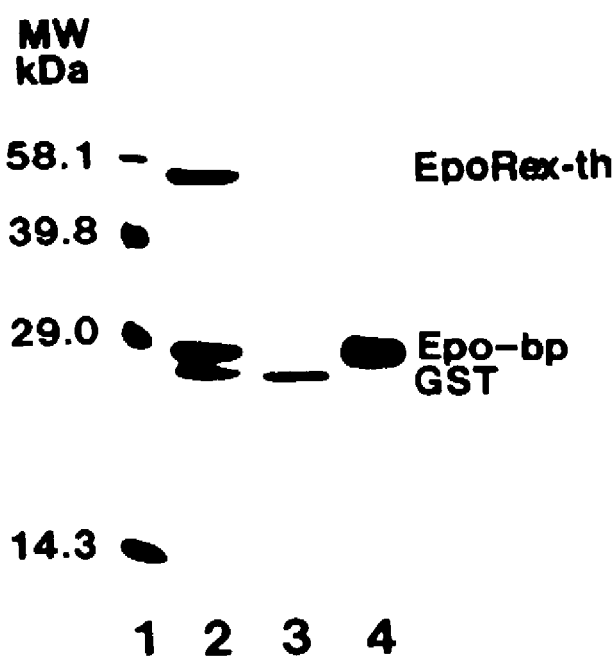
FIG. 4 is a Western blot, showing binding of sheep anti-Epo-bp antibody to Epo-bp.

Sheep anti-Epo-bp serum was analyzed for binding to purified Epo-bp by Western blotting as described in Sambrook et al., *Molecular Cloning*, 2nd Ed., Cold Spring Harbor Laboratory Press, 1989 and in Western blotting protocols provided by the ECL manufacturer, Amersham Co., Arlington Heights, Ill. Following thrombin cleavage, EpoRex-th and Epo-bp were separated electrophoretically on an SDS-PAGE gel. The gel was then blotted onto nitrocellulose (Schleicher and Schuell Co., Keene, N.H.). Sheep anti-Epo-bp serum was added to the nitrocellulose in Blotto (for 1 liter: 80 g non-fat dry milk, 30 ml 5M NaCl, 10 ml 2M Tris-HCl, pH 7.5 and 0.05% Tween-20) at a 1:2000 dilution and incubated at room temperature for 1 hour with gentle agitation. After rinsing off the first antibody, a second reagent, biotinylated rabbit anti-immunoglobulin anti-sheep (1:10,000 dilution) antibody was added to the nitrocellulose in Blotto, and incubated at room temperature for another 1 hour with rocking. Horseradish peroxidase-avidin (1:10,000 dilution) was added and the mixture incubated at room temperature for 45 min. After soaking the washed nitrocellulose briefly in chemiluminescence (ECL) reagents, wet blots were exposed immediately on KODAK X-ray film. FIG. 4 shows a photograph of the Western blot, with the lanes having the following proteins applied: Lane 1, molecular weight standards; Lane 2, thrombin digested EpoRex-th; Lane 3, GST; Lane 4, purified Epo-bp. As shown in lane 4 of FIG. 4, purified Epo-bp was detected by a 1:2000 dilution of anti-Epo-bp antibody. The apparent molecular weight of the purified Epo-bp was about 29 kDa.

EXAMPLE 6

Binding of Epo to Epo-bp

Ligand binding of Epo to Epo-bp and effects of Epo concentration on binding are taught in this example.

Epo-bp beads were prepared by adding 60 $\mu$g/ml Epo-bp to washed Affigel 15 agarose beads in PBS, with a final concentration of approximately 30 $\mu$g of protein per 1 ml of Epo-bp beads. The mixture was incubated at room temperature for 2 hours on a rotating platform. After washing 3 times with ice cold PBS buffer, the pellet was resuspended in 1 ml of PBS buffer. For binding assays, 30 $\mu$l of the final suspension (approximately 1.0 $\mu$g of Epo-bp) were admixed with various concentrations of $^{125}$I-Epo and incubated for 1 hour at room temperature while resuspending every 5 min with a pipet. At the end of the incubation, 1 ml of ice cold PBS buffer was added to wash out unreacted $^{125}$I-Epo and the wash was repeated twice more. The reacted beads were counted by a gamma counter. Proteins smaller than the intact Epo-bp from trypsin digested extracts (see below) were also applied in the same way to test any effect on ligand binding. Nonspecific binding was measured by the same method except the mixture was preincubated with a 200-fold excess of unlabeled Epo for 1 hour prior to adding labeled Epo.

Figure 5:
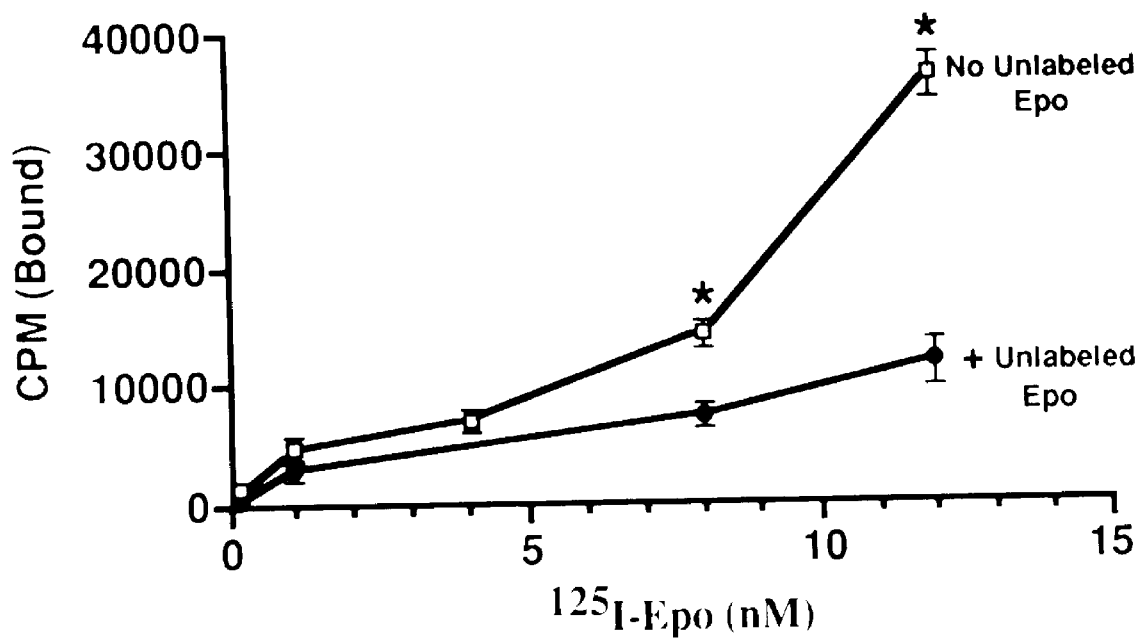
FIG. 5 shows the binding of various concentrations of human $^{125}$I-Epo to Epo-bp, in the presence and absence of unlabeled Epo.

Binding of Epo-bp to Epo is shown in FIG. 5. Each point in FIG. 5 is the mean of 2–4 samples. Data are expressed as mean±SEM. A p value of less than 0.05 was considered significant. Results were analysed with the two-tailed Student t-test. The specific binding activity of Epo to Epo-bp dramatically increased as Epo concentration increased; the binding tripled from 8 nM to 12 nM $^{125}$I-Epo. Apparent saturation of Epo binding occurred at 12 nM. This was also confirmed in the unreacted supernatant of $^{125}$I-Epo. Binding of $^{125}$I-Epo to Epo-bp was significantly inhibited in the presence of unlabeled Epo at concentrations of 8 nM and higher of $^{125}$I-Epo (p<0.0001 in both comparisons). Non-specific binding was somewhat higher than expected. It had been expected that the excess unlabeled Epo might eliminate $^{125}$I-Epo binding completely because of the sensitivity and specificity of Epo binding to Epo-bp shown in Western blots and binding assays.

Figure 6:
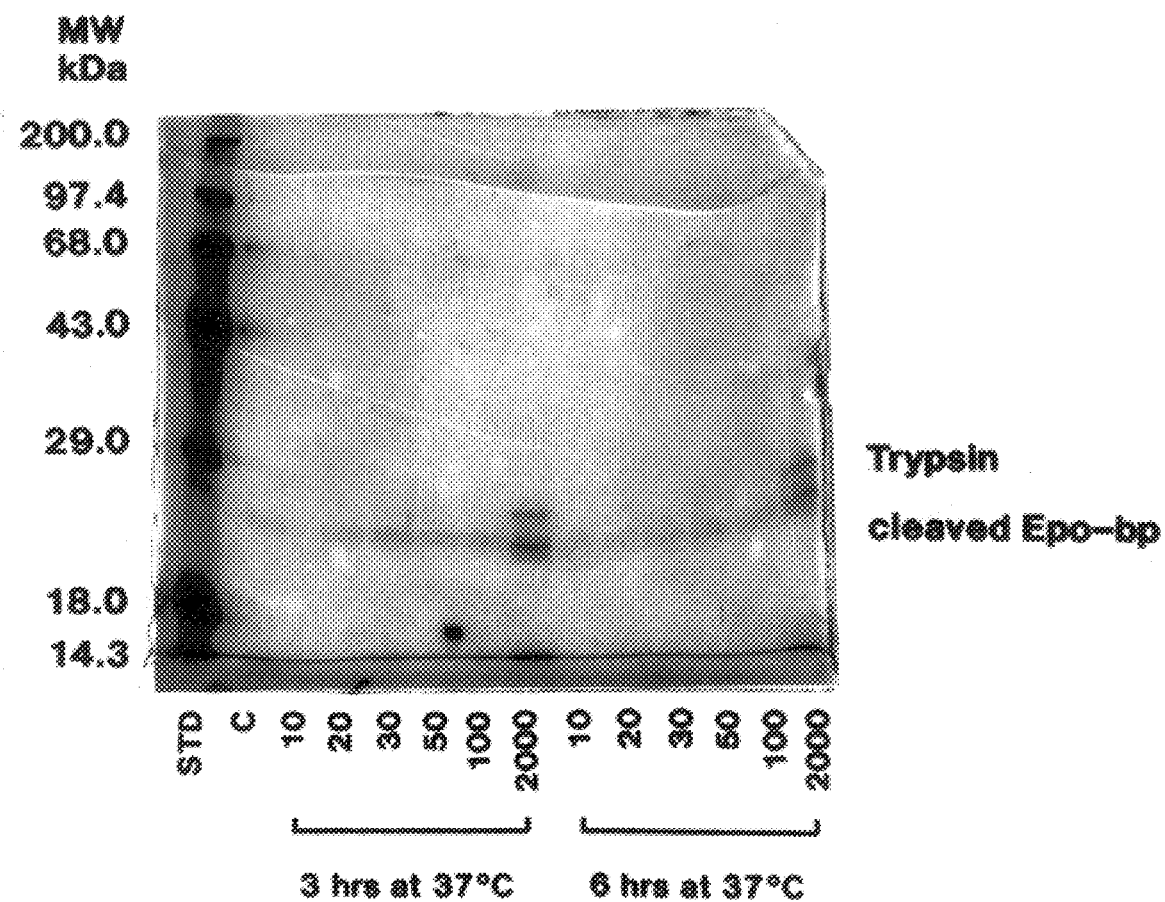
FIG. 6 is a photograph of a Coomassie blue stained polyacrylamide gel, showing the polypeptide bands observed after trypsin digestion of Epo-bp.

Trypsin digestion experiments were performed to find a minimum sequence of Epo-bp involved in ligand binding. There are several arginine and lysine sites in the Epo receptor protein, which may be specific sites for trypsin digestion. Trypsin digestion of Epo-bp was carried out at 10, 20, 30, 50, 100 $\mu$g and 2 mg of trypsin per 5 $\mu$g of Epo-bp in a total volume of 200 $\mu$g in PBS, pH 6.7 at 37° C. for 3 or 6 hours. The reaction was stopped by adding the same volume of 2N acetic acid or by boiling. As shown in FIG. 6, Epo-bp was cleaved effectively when 20 $\mu$g or more of trypsin was present. Trypsin is visible as a 23.2 kDa protein band in the lane having 2 mg of trypsin. The trypsin digested Epo-bp is visible as a 20-kDa protein. In FIG. 6, Lane 1 contains standard molecular weight markers; lane 2 is a control; lanes 3–8 represent digestions at concentrations of 10, 20 30, 50, 100 $\mu$g and 2 mg trypsin, respectively at 37° C. for 3 hours; lanes 9–14 represent the same concentrations of trypsin incubated at 37° C. for 6 hours.

Since uncut Epo-bp is aproximately 30 kDa, gel filtration chromatography using Pharmacia Sephadex G-50 (MW$\leq$30,000) was applied to separate protein components of size$\leq$30,000 molecular weight from the total mixture. A powdered form of Sephadex G-50 was hydrated and washed several times with isotonic PBS to wash out preservatives. Trypsin digested EpoRex-th was applied to the top of the gel column in a total volume of 0.2 ml in PBS. The column was centrifuged at 2,000 x g for 4 min at room temperature in a swinging-bucket rotor. The first effluent was collected from the bottom of the syringe (~0.2 ml) into a decapped microfuge tube. This effluent contains proteins having a size larger than Epo-bp. Another 0.2 ml of PBS buffer was added to the column and a second eluate collected into a new decapped microfuge by recentrifuging for 10 min. This step was repeated twice. The second eluate was applied to an Epo-agarose column and peak fractions were examined by SDS-PAGE gels and Western blotting. The final product of Epo-bp, as a result of trypsin digestion, was approximately 20 kDa, shown in FIG. 6. The antibody did not recognize the cleaved Epo-bp. Thus, deletion of 30 amino acids from Epo-bp by trypsin digestion completely eliminated recognition by antibodies to Epo-bp, as verified by Western blotting.

The foregoing detailed description has been provided for a better understanding of the invention only and no unnecessary limitation should be understood therefrom as some modifications will be apparent to those skilled in the art without deviating from the spirit and scope of the appended claims.

I claim:

1. An expression vector comprising a coding sequence for a fusion protein, said coding sequence comprising:
   (a) a first nucleotide sequence capable of expressing a polypeptide having a thrombin proteolytic cleavage site at the carboxyl terminus of said polypeptide, and;
   (b) a second nucleotide sequence consisting of about nucleotides 73 to about 750 of a full length human erythropoietin receptor cDNA coding sequence (SEQ ID NO: 5), said second sequence positioned 3' to said thrombin proteolytic cleavage site and translationally fused to said first sequence.

2. The expression vector of claim 1, wherein said vector is capable of expressing said fusion protein in *Escherichia coli*.

3. A method for obtaining a substantially pure human erythropoietin receptor polypeptide consisting of about amino acid 25 to about amino acid 250 of the full length human erythropoietin receptor protein (SEQ ID NO: 5), said human erythropoietin receptor polypeptide being capable of binding erythropoietin, comprising:
   (a) providing the purified fusion protein of claim 2;
   (b) treating said fusion protein with thrombin under conditions allowing cleavage of said polypeptide from said fusion protein, to form a digest mixture;
   (c) adding said digest mixture to a solid phase reagent having erythropoietin coupled thereto, under conditions allowing binding of said polypeptide with said solid phase reagent, to form a polypeptide-solid phase composition;
   (d) washing said polypeptide-solid phase composition to remove unbound material; and
   (e) eluting said polypeptide from said polypeptide-solid phase composition.

4. A purified fusion protein consisting of:
   (a) a first polypeptide segment having an amino terminus and a carboxyl terminus, said segment having a thrombin proteolytic cleavage site at said carboxyl terminus; and
   (b) a second polypeptide segment consisting of about amino acid 25 to amino acid 250 of a full length human erythropoietin receptor protein (SEQ ID NO: 5), said second polypeptide segment being covalently coupled to said carboxyl terminus of said first polypeptide segment.

* * * * *

UNITED STATES PATENT AND TRADEMARK OFFICE
CERTIFICATE OF CORRECTION

PATENT NO.   : 5,843,726
DATED        : DEC. 1, 1998
INVENTOR(S)  : JONG Y. LEE

It is certified that error appears in the above-identified patent and that said Letters Patent is hereby corrected as shown below:

In column 2, line 60, "SEQ ID NO:5" should read --SEQ ID NO:4--.
Claim 1:
Lines 52-53, "SEQ ID NO:5" should read --SEQ ID NO:4--.

Signed and Sealed this

Nineteenth Day of September, 2000

Attest:

Q. TODD DICKINSON

*Attesting Officer*            *Director of Patents and Trademarks*